United States Patent [19]

Miccoli et al.

[11] Patent Number: 5,070,079

[45] Date of Patent: Dec. 3, 1991

[54] PHARMACEUTICAL COMPOSITIONS CONTAINING CYTIDINE MONOPHOSPHATE OF 5-ACETAMIDO-3-, 5-D-DEOXY-D-GLYCERO-D-GALACTO-NONULOSAMIC ACID

[75] Inventors: Pietro Miccoli, Triest; Enio Decorté, Aiello del Friuli, both of Italy

[73] Assignee: CRC-Compagnia di Ricerca Chimica S.p.A., S. Giovanni al Natisone, Italy

[21] Appl. No.: 560,239

[22] Filed: Jul. 23, 1990

Related U.S. Application Data

[60] Division of Ser. No. 228,828, Aug. 3, 1988, abandoned, which is a continuation of Ser. No. 73,751, Jul. 10, 1987, abandoned, which is a division of Ser. No. 584,805, Feb. 29, 1984, Pat. No. 4,704,361.

[30] Foreign Application Priority Data

Mar. 1, 1983 [IT] Italy .............................. 83341 A/83
Apr. 20, 1983 [IT] Italy .............................. 83371 A/83

[51] Int. Cl.$^5$ ............................................. A61K 31/70
[52] U.S. Cl. ..................................... 514/51; 514/824; 514/907
[58] Field of Search .......................... 514/51, 824, 907

[56] References Cited

U.S. PATENT DOCUMENTS 4,100,271  7/1978  Krezanoski ......................... 424/78
4,593,091  6/1986  della Valle et al. ................ 536/123

OTHER PUBLICATIONS

Hultsch et al., Chem. Abst. 77:57997z, 1972.
Corfield et al., Chem. Abst. 91:86110z, 1979.

*Primary Examiner*—John W. Rollins
*Attorney, Agent, or Firm*—Hopgood, Calimafde, Kalil, Blaustein & Judlowe

[57] ABSTRACT

The invention relates to pharmaceutical compositions for use in the therapy of pathological states related to disturbances of the nervous stimulus in the central (CNS) and peripheral (PNS) nervous system containing as an active substance the cytidine monophosphate of 5-acetamido-3,5-dideoxy-D-glycero-D-galactonon ulosaminic acid. Moreover the invention relates to an improved method for preparing said compound by the condensation of cytidine triphosphate (CTP) with N-acetylneuraminic acid (NANA), catalyzed by the enzyme CMP-transferase (CMP-acylneuraminate synthase) (EC 2.7.7.43).

2 Claims, No Drawings

PHARMACEUTICAL COMPOSITIONS CONTAINING CYTIDINE MONOPHOSPHATE OF 5-ACETAMIDO-3-, 5-D-DEOXY-D-GLYCERO-D-GALACTO-NONULOSAMIC ACID

This application is a division of Ser. No. 07/228,828 filed 08/03/88, now abandoned, which is a continuation of Ser. No. 07/073,751 filed 07/10/87, now abandoned, which is a division of Ser. No. 06/584,805, filed 02/29/84, now U.S. Pat. No. 4,704,361.

The present invention relates to pharmaceutical compositions for use in the therapy of pathological states related to disturbances of the nervous stimulus in the central (CNS) and peripheral (PNS) nervous system containing as an active substance the cytidine monophosphate of 5-acetamido-3,5-dideoxy-D-glycero-D-galactononulosaminic acid. Moreover the invention relates to an improved method for preparing said compound.

It is already known that the cytidine monophosphate of 5-acetamido-3,5-dideoxy-5-glycero-D-galactononulosaminic acid—usually abbreviated as CMP-NANA or CMP-NeuAc—having the following formula:

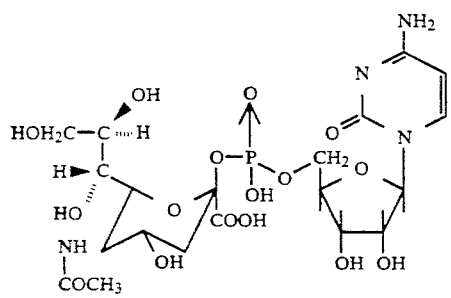

represents the biologically active form of 5-acetamido-3,5-dideoxy-D-glycero-D-galactononulosaminic acid (usually called N-acetyl-neuraminic acid and abbreviated as NANA) and that this compound is the product of various anabolic processes in the living organisms.

NANA represents the physiologically active part of the molecules found in the membranes (gangliosides and glycoproteins), that are generally structured in the way to be able to receive and to transmit all necessary informations for the functioning of the cell (see e.g. R. W. Jeanloz et al. The Biological Role of Sialic Acid at the Surface of the Cell, in Biological Roles of Sialic Acid, A. Rosenberg et al. Eds., Plenum Press, pp 201-227, 1976).

It is also well known, see for example S. Roseman, Proc. Natl. Acad. Sci. U.S. 48, 437-41 (1962); N. Sharon, Complex Carbohydrates, Addison-Wesley, Publishing Co., London-Amsterdam, pp. 150-53, 1979, to prepare CMP-NANA by a biochemical method according to the following reaction scheme:

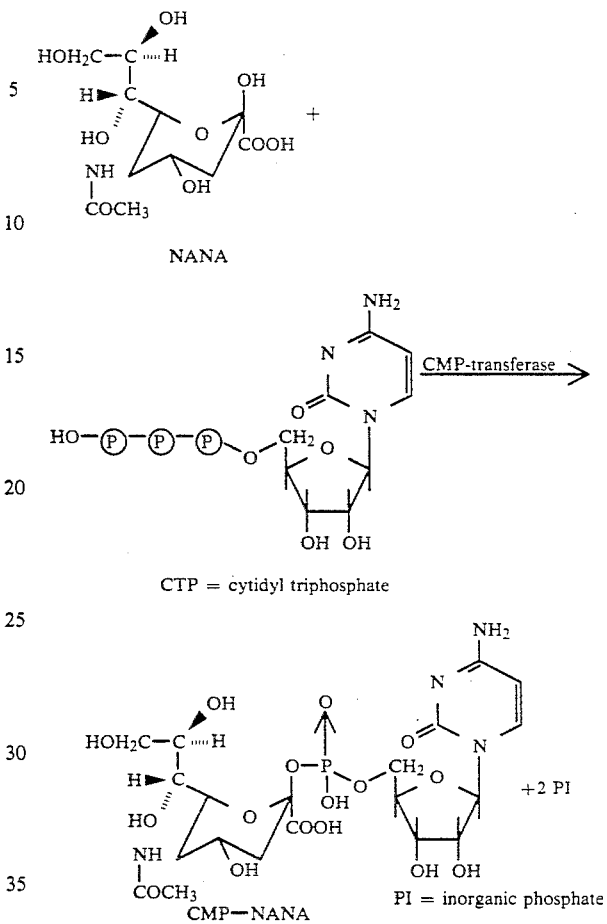

From B. Bendiak et al., Can. J. Biochem. 59, 171-180 (1981) and A. Preti et al., J. Neurochem. 35, 281-296 (1980) it is also known that the CMP-NANA represents the physiological substrate of the enzyme sialyl transferase, that consents its incorporation into the already indicated subunits of the biological membrane, i.e. gangliosides and glycoproteins.

As indicated in the reaction (I), during the synthesis of the active form of NANA, the energy of the two highly reactive bonds in the CTP is consumed. On the other hand, N-acetyl neuraminic acid can only in its active form be incorporated into the membrane. (see e.g. A. Arce et al., Arch. Biochem. Biophys. 116, 52-58 (1966)).

It is important to note that beside the normal turnover of the components in the membrane, functioning the membrane is connected with a repeating attachment and detachment of the NANA residues. It is actually the variation of the negative charge that NANA imparts to the surface of the membrane, which modulates its functional activity. (see e.g. R. Jbernacki et al., The Glycoconjugates vol. IV part B, M. I. Horowitz E., Academic Press, pp. 256-261, 1982; S. Ng et al., The Natural Occurence of Sialic Acid, in Biological Roles of Sialic Acid, A. Rosenberg et al., Eds, Plenum Press, pp. 59-86, 1976).

It has also been proposed (see. Ital. pat. appln. 26323A/75) to use for the treatment of nervous disorders gangliosides, as the mixture obtained on extraction from the natural sources, i.e. from the nervous tissue of the mammals that contains monodi-tri-and tetra-N-acetyl neuraminic gangliosides.

However, such therapeutical methods possess some drawbacks, as e.g.:

a. The composition of the mixture of gangliosides is difficult to control and requires sophisticated instrumentation;

b. low chemical stability of the biopolymers, as are the gangliosides, provokes their limited "shelf life" as the pharmaceutical speciality; this rises therapeutical risks, i.e. various non-controllable side effects;

c. the gangliosides, being biopolymers of the high formula weight (approx. 1500) manifest antigenic properties (see e.g. J. T. Rick et al., Develop. Med. Child Neurol. 22, 719–724 (1980).

Until now CMP-NANA was never used in the form of a pharmaceutical composition for the therapy of pathological states related to disturbances of the nervous stimulus in the central (CNS) and peripheral (PNS) nervous system.

It has now been found that CMP-NANA (I) is an extremely valuable compound for the treatment of disturbances of the nervous stimulus in the central (CNS) or peripheral (PNS) nervous system, for example: alterations of the nervous transmissions at the CNS or PNS level, traumatic and toxic damages of the peripheric nerves, disturbances of the memory in the consequence of pathological events as the Huntington's Corea, senile dementia, confusional states of artheriosclerotic or vascular origin, optical retrobulbar neurites, paralysis of the oculomotoric nerves, neuralgias of trigeminus, paralysis of the facial or the Bell's nerve, Garcin's syndrome, Guillan Barrè's syndrome, radiolites, diabetical and alcoholical polyneurites, obstetrical paralysis, motoneuronical diseases, lateral amiotrofic sclerosis, myelopatic muscular atrophy, progressive bulbar paralysis, serious miastenia, muscular distrophy, disturbance of the conscience as the state of confusion, cerebral commotions, results of the cranial traums, cerebral vascular distrubs and thromboses.

It has also been found that CMP-NANA (I) can be obtained by two new enzymatic methods, both of which are based on the condensation of cytidine triphosphate (CTP) with N-acetylneuraminic acid (NANA) catalyzed by the enzyme CMP-acylneuraminate synthase (EC 2.7.7.43).

In the first new method (A), the condensation of CTP with NANA is catalyzed by the enzyme CMP-acylneuraminate synthase (EC 2.7.7.43), either cell-free, soluble or immobilized on a suitable solid carrier from various natural sources in the presence of BrCN, which allows chemical bonding between proteinic structure of enzyme and solid support, a thiocarboxylic acid stabilizer and/or a nitroimidazole stabilizer.

In the second new method (B) the condensation of CTP with NANA is catalyzed by the enzyme CMP-acylneuraminate synthase (EC 2.7.7.43) isolated by the E. coli strain CRC 1482, deposited in 'Deutsche Sammlung Von Mikroorganismen' Gesellschaft Fuer Biotechnologische Forschung GMBH, Goettingen (BRD) on Feb. 27, 1984 under the deposition number 2904'.

The second method (B) can also optionally be accomplished in the presence of a thiocarboxylic acid stabilizer and/or nitro-imidazole stabilizer and/or under the conditions of method (A).

Accordingly one object of the invention is a pharmaceutical composition for use in the therapy of pathological states related to disturbances of the nervous stimulus in the central (CNS) and peripheral (PNS) nervous system comprising the cytidine monophosphate of 5-acetamido-3,5-dideoxy-D-glycero-D-galactononulosaminic acid (I)

Another object of the invention is a method for preparing (I), by the condensation of cytidine triphosphate (CTP) with N-acetyl-neuraminic acid (NANA) catalyzed by the enzyme CMP-acylneuraminate synthase (EC 2.7.7.43) characterized in that (A) the condensation is accomplished in the presence of a thiocarboxylic acid stabilizer and/or a nitro-imidazole stabilizer or (B) that the condensation is accomplished by the enzyme CMP-acylneuraminate synthase (EC 2.7.7.43) isolated by the E. coli strain CRC 1482.

The invention avoids most of the problems related to the therapeutic usage of gangliosides, besides it allows following advantages:

a. the active form of NANA, i.e. CMP-NANA, is directly supplied to the organism, particularly in the certain pathological states, when their cellular turnover requires higher supply of this molecule, e.g. in the moment of regeneration of the nerve. In fact, the gangliosides and the glycoproteins, wherein NANA is going to be incorporated, are involved in all cell to cell recognition phenomena, as well as between the cell and the environment, so-called social cell behaviour;

b. the CMP-NANA is a chemically well defined molecule, available also via enzymatic synthesis in vitro in the highest degree of the purity;

c. chemical purity and biological activity level of CMP-NANA could be determined, or controlled, using simple chemical tests and enzymatic in vitro techniques, already described (see e.g. R. W. Leedeen et al., Chemistry and Analysis of Sialic Acid., in Biological Roles of Sialic Acid, A. Rosenberg et al. Eds, Plenum Press, pp. 1–48, 1976);

d. it is definitely proved that CMP-NANA is incorporated in vivo into gangliosides and glycoproteins (for the complete review see The Glycoconjugates Vol. IV part. B, M. I. Horowitz Ed., Academic Press, 1982; E. J. McGuire, Anabolic Reactions involving Sialic Acids, in Biological Roles of Sialic Acid, A. Rosenberg et al. Eds, Plenum Press, pp. 123–158, 1976);

e. the CMP-NANA, being a molecule of the dimensions substantially reduced in relation to the gangliosides, does not manifest any antigenic properties, that have been noticed for the latter compounds or related macromolecules;

f. the CMP-NANA, being an endogeneous molecule, possesses very low toxicity for the man. Our results, obtained for the albino rats of the weight $20 \pm 1$ g divided into two groups of 30 in each, and two control groups, have demonstrated $LD_{50}$ of 900 mg/kg for the intraperitoneal application, and of 2400 mg/kg for the per os application.

In the new method of preparing the cytidine monophosphate of 5-acetamido-3,5-dideoxy-D-glycero-D-galactononulosaminic acid (I) by the condensation of (CTP) and (NANA) the preferred millimolar ratio CTP/NANA is from 3.0–5.0:1.0 mmol. The preferred pH is between 8.5 and 8.8. Preferably the condensation is accomplished at a temperature from 30°–40° C. and preferably from 1 to 4 hours. According to a preferred embodiment the thiocarboxylic acid and nitroimidazole stabilizers are used in an amount from 0.5–2.0 mM per mMol of CTP or per liter of total volume.

As a thiocarboxylic acid stabilizer the most different thiocarboxylic acids or mercaptocarboxylic acids can be used, for example acids of the formula HS(CH$_2$)$_n$COOH, wherein n represents an integer from 1 to 5, like mercaptoacetic acid or β-thiopropionic acid or acids of the given formula, in which a methylene group —H$_2$— is substituted by an alkyl group, for example (+)-β-thio-α-methyl-propionic acid and (+)-β-thio-α-ethylpropionic acid.

As a nitro-imidazole stabilizer the most different nitro-imidazoles and nitro-imidazole derivatives can be used for example those of the following formula:

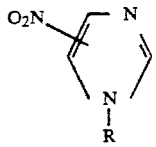

wherein the nitro group may be in the 2-, 4- or 5-position and R represents hydrogen or an optionally substituted alkyl group, for example an hydroxyethyl or β-ethylthioethyl group. Typical useful nitro-imidazoles are: 2-nitro-imidazole; 2-methyl-5-nitro-1-hydroxyethylimidazole and 2-methyl-5-nitro-1-β-ethylthioethylimidazole.

The thiocarboxylic acids act as antioxidants. Because of their high hydrophilicity and buffering properties they are preferred over similar compounds like alkylthiols.

The use of the nitroimidazols is especially advantageous because of their bacteriostatic activity.

Preferably the reaction product (I) is isolated by ion exchange chromatography, and/or by chromatography on Sephadex columns using linear gradient of buffers that have pH between 8.2–8.6 as e.g. triethylamine/sodium bicarbonate, or aqueous ammonia 0.5–1.5 mM solution, and working at 0°–6° C.

In the methods according to the invention the enzyme CMP-acyl-neuraminate synthase (EC 2.7.7.43), for which also the name CMP-transferase is used, can be used either cell-free, soluble or immobilized on a suitable solid carrier, or present in the bacterial cell of the strain Escherichia coli CRC-1482. The cell-free enzyme can be isolated according to known isolation procedures as described for example by F. A. Troy et al., J. Biol. Chem. 249 (1974) 156; I. K. Vijay, J. Biol. Chem. 250 (1975) 164; J. Haverkamp et al., Hoppe-Seyler's Z. Physiol. Chem. 360 (1979) 159 from homogenized animal tissues, for example from frog liver (from Rana Esculenta), calf brain, hog, sheep or bovine submaxillary glands in the presence of a thiocarboxylic acid or mercaptocarboxylic acid of the same type as used as a thiocarboxylic stabilizer as mentioned above, e.g. β-thiopropionic acid or (+)-β-thio-α-ethylpropionic acid, in a concentration from 0.5 to 2.0 mM per liter of total volume maintaining the pH between 7.1–7.2 and at temperatures between 0°–4° C., while in the cases where immobilized enzyme EC 2.7.7.43 is used, its immobilization is performed for example by binding on the suitable solid carrier, as for example Sepharose.

Preferably the immobilization is accomplished in the presence of appropiate stabilizers at a pH from 8.5 to 9.0. Useful stabilizers are for example bromocyanide (CNBr) as well as the most different thiocarboxylic acid stabilizers and nitroimidazoles and nitroimidazole derivatives, already mentioned above as additives for the CTP-NANA-condensation reaction. The nitroimidazoles and derivatives thereof function as antioxydation stabilizers as well as bactericide.

The following examples are to illustrate the invention.

A) Preparation Method

EXAMPLE 1

Preparation of cytidine monophosphate of 5-acetamido-3,5-dideoxy-D-glycero-D-galactononulosaminic acid (I) catalysed by the cell-free CMP-acylneuramincate synthase from the frog liver Frog liver (200 g, from Rana Esculenta) was homogenized in an Ultra-Turrax homogenizer at 90s using equal volume of 80 mM Tris/HCl buffer pH 7.2, containing 1 mM of β-thio-propionic acid, and under cooling in an ice bath. The homogenate was centrifuged (90000×g, 30 min.), supernatant collected and centrifuged for another 60 min. at 90000×g. The second supernatant (ca. 250 ml) was applied on a DEAE-Sephadex A-50 column previously equilibrated with 80 mM Tris/HCl buffer of a pH 7.2, containing 1 mM of β-thio-propionic acid. After washing with the same buffer, about 1000–1200 ml, a 0–1.5M sodium chloride linear gradient in the same buffer was used. After 2500 ml eluation all fractions containing enzyme were eluated. They were collected (~600 ml), ultrafiltered under nitrogen, and the final volume (120 ml) exhibited activity ranging between 0.3–0.6 units/ml (1 unit of activity forms 1 μmol of I/min).

A 20 ml aliquot (containing about 8000 units of the enzyme) of the enzyme, CTP (4–5 mmol), N-acetylneuraminic acid (1 mmol) were added in portions, during 2 hours, to the solution (200 ml) of Tris-buffer, Mg$^{+2}$, and β-thio-propionic acid. The last three components were present in the concentrations 0.4, 0.04, and 0.002M, respectively. The mixture was incubated at 36±0.2° C. for 6 hours, then diluted 8 times with water and rised slowly through a column of Dowex 1×4, bicarbonate form, 50–100 mesh (0.6 l resin/mmol of I). First washing was performed with 1 mM ammonium hydroxide, then with 3–4 vol. of a line gradient from 0.02–2.0M triethylammonium hydrogencarbonate, pH 7.8. Fractions containing I (determined quantitatively according to E. L. Kean et al., "Methods in Enzymol." 8, 208 (1966) were pooled and lyophilized. The pure I exhibited R$_f$~0.2 on tlc (0.1 mm cellulose sheets (Merck) with 96% ethanol-1M ammonium acetate, pH 7.4 (7.2:2.8 and as white to bright-yellow powder could be stored at −10° C. for at least one year. The yield was 85%, calculated on N-acetylneuraminic acid.

EXAMPLE 2

Preparation of I catalysed by the cell-free CMP-acylneuraminic synthase from the hog submaxillary gland Thin slices from the frozen hog submaxillary glands (0.5 kg) were gently shaken for 2 hours in 1 l of 0.15M phosphate buffer of a pH 7.8. After centrifugation at 45000×g the supernatant fluid was applied to a DEAE Sephadex A-50 column, previously equilibrated with 80 mM Tris/HCl buffer, pH 7.2. After the column was washed with the same buffer, the enzyme was eluated with 0–1.5M sodium chloride linear gradient in the same buffer. The DEAE-fractions were treated with calcium phosphate gel. 3–5 g of gel per g of protein were used. After shaking for 0.5 hours at 0°–6° C. (all other operations were performed in the same temperature interval), the suspension was centrifuged at 9500×g, the precipitate was washed (2×Tris buffer pH 7.2, 2×0.01M phosphate buffer, pH 7.6), and the enzyme was finally eluated from the gel by washing with 0.1M phosphate buffer of a pH 7.8.

The enzyme thus obtained was used for the preparation of I as described in Example 1. Crude I thus obtained (78% yield) was ulteriorly purified, after chromatography on Dowex 1×4, bicarbonate form, by gel filtration on Sephadex G-10 or G-25, using 0.1 mM ammonium hydroxide. The column size was 3×120 cm for up to 0.3 mmol of I samples, and the flow rate was 10-15 ml/hr. Fractions containing I (60% yield) were pooled, lyophilized and stored at −10° C. Pure I exhibited $[\alpha]_D = -11.5°$ (c=0.2, water), and was found to be >98% pure by acid hydrolysis - thiobarbituric acid assay, according to E. L. Kean et al., Biol. Chem. 241, 5643 (1966).

EXAMPLE 3

Preparation of I catalyzed by the cell-free, on Sepharose 4B immobilized CMP-acylneuraminate synthase from the frog liver Pure enzyme has been prepared as described in Example 1. The enzyme extract (5 ml, containing 5-6 units/ml) was diluted with 100 mM bicarbonate, pH 8.2, (1:2), and mixed at 0° C. with the slurry of Sepharose 4B, activated with cyanogen bromide (according to A. P. Corfield et al., Biochem. J. 177, 1 (1979)). After shaking for 12 hours at 4° C., the gel was filtered, washed with water and 2N sodium chloride, and again with water. The gel was stored at 0°-6° C. in 80 mM Tris)HCl, containing 0.6 mM of $(\pm)\beta$-thio-$\beta$-methyl-propionic acid, and 2 mM of 2-nitroimidazole as bactericide. The immobilized enzyme thus prepared (100 units) was used for the catalytic preparation of I. To this aim 6 mmol of N-acetylneuraminic acid, 1.5 mmol of CTP, 0.1 mol of Tris, 80 mmol of $Mg^{+2}$ ions, and 0.1 mmol of $(\pm)$-$\beta$-thio-$\beta$-methyl-propionic acid, in the total volume of 1.5-2.0 pH 8.2-8.4, were incubated at 36° C. for 4 hours. The incubation was performed in a Biogen continuous culture apparatus (American Sterilizer), the pH was controlled by the automatic addition of 2% sodium hydroxide, while N-acetylneuraminic acid was added in small portions during the first two hours. After completion of the reaction the gel was filtered off, and washed with water. The collected washings were applied to the DOWEX 1×8 column, bicarbonate form. Using a linear gradient 0-1.5M triethylamine/$NaHCO_3$ buffer, pH 8.4, at the flow rate 0.6 ml/min, the compound I (88%) was eluated. Pure I was separated from contaminating CMP by the second chromatography on a column of Sephadex G-25, eluated with 1 mM aqueous ammonia, freeze-dried, and stored at −10° C. The yield was 58%.

$[\alpha]_D = -11.8°$ (c=0.2, water). A sample was maintained at pH 1 for 10 min at room temperature, affording CMP and N-acetylneuraminic acid (1.0:1.0 mol), with $R_f$ values 0.05, and 0.5 respectively (solvent system, and the conditions as described in the Example 1).

EXAMPLE 4

Preparation of I catalysed by the E. coli CRC-1482 strain

An *Escherichia coli* strain has been developed by repeated selection of the cultures with maximal CMP-acylneuraminate synthase activity. The cultures were grown on a medium of the following composition (per liter of the total volume): 15 g agar, 6 g yeast extract, 2 g glycine, 4 g dextrose, 0.2 g $\beta$-thiopropionic acid, 4 g disodium hydrogen phosphate, 2 g monosodium dihydrogen phosphate and 0.2 g trimethylbenzyl ammonium hydroxide. All ingredients were previously dissolved in 20-50 ml of water and sterilized separately. Small scale experiments were performed on a rotary shaker (new Brunswich) at 240 rpm. (For the selection experiments samples of the cultures (100 ml) have been tested by extraction of the cells and determination of I as described in the following paragraph for in bulk production of I).

Inoculation for large-scale production has been performed by repeated transfer of the growing cells into 10-15 volumes of the fresh medium. Final fermentations were performed in 20-40 volumes at 36° C. for 4 hours under continuous aeration with sterile air. Various antifoaming agents were used at this stage to eliminate or reduce foaming, while pH was maintained at 8.2-8.3 by continuous addition of 5% sodium hydroxide. When the cultures reached their stationary phase, they have been centrifuged at 90000×g at 0° C., and the cell paste (about 100-150/10 l of the fermentation volume) was frozen. To this paste acetone was added (about 1.5-2 l/100 g of the paste), at 0° C. and the resulting precipitate was collected on a filter, washed with acetone and dried. The dry powder was slurried in an ethanol-water mixture (4.0:1.0), stirred for 3-4 hours, centrifuged at 90000×g, and washed (2×) with the same solvent mixture. From the combined extracts and washings pure I was isolated as described in Example 1. The yields on I was 15-20% of the total nucleotides adsorbed by the ion exchange resin.

B) Therapeutical Application

EXAMPLE 1

Administration of CMP-NANA to rats

The study has been performed with 16 couples of the rats Charles River in their reproductive age, selected by uniform weight. On the third day of gestation they have been arbitrarily divided into 4 groups. The two first groups have been fed with a semisynthetic diet that contained 10% of casein. Dietetic treatment have been continued during the entire periods of gestation and nursing.

Between the 14th and the 21st day of the life, the puppies of the 2nd and the 4th group have been treated with 20 mg/kg of CMP-NANA (Sigma Chemical Co.) i.p., the 1st and the 3rd group have been treated with the equal volume of physiological solution.

On the 21st day two male puppies from each group have been fixed on the holed table and for 20 minutes placed under the open field experiment. The periods related to the explorative activity have been observed and quantified. At the end of the experiment, the animals have been sacrificed by decapitation, and their brains have been removed and examined for the content of the gangliosides (extractions performed by the method of G. Tettamanti et al., Biochim. Biophys. Acta 296, 160-170 (1973) as well as of the glycoproteins (extractions by the method of B. Berra et al., in Membranes in Tumor Growth, Galeotti et al., Eds., Elsevier, pp. 81-87, 1982; F. Omodeo Salè et al., Cell Mol. Biol. 27, 455-458, 1981).

In both cases the content of NANA has been determined.

Table 1 demonstrates that in the group of the rats fed with normal proteinic diet, as well as in the group treated with a hypoproteinic diet, the treatment with CMP-NANA has inhanced in statistically significant manner, both the explorative activity as well as the NANA content in the cerebral gangliosides and glycoproteins.

TABLE 1

Explorative activity and cerebral content of the gangliosides and glycoproteins in the rats on the 21st day of the life, well fed with the hypoproteinic diet either treated or non-treated by CMP-NANA. Medium values are given per group in percents, assuming 100% medium for the 2nd group.

|  | Explorative activity | Cerebral gangliosides | Cerebral glycoproteins |
|---|---|---|---|
| Group 1: 20% of casein | 47 | 75 | 79 |
| Group 2: 20% casein + CMP-NANA | 100+ | 100+ | 100+ |
| Group 3: 10% casein | 12 | 41 | 69 |
| Group 4: 10% casein + CMP-NANA | 52+ | 68+ | 75+ |

+The differences between the CMP-NANA treatment and non-treatment that is statistically significant ($p < 0.01-0.001$) evaluated by the Student's "t" test.

EXAMPLE 2

Levels of cerebral gangliosides of the rat following the injuries rised by kainic acid Male rats, Charles River CD, body weight of 180–200 g, have been divided into 4 groups, each group having 20 animals. The first group has been classified as the control group, the second group has been treated with physiological solution, the third group has been treated with kainic acid and the fourth group has been treated with CMP-NANA (20 mg/kg/day, i.p.) and kainic acid.

The treatment with CMP-NANA has been started one week before the treatment with kainic acid and has been continued until the animals have been sacrificed.

The animals have been anesthetized with pentobarbital (60 mg/kg i.p.) and then treated with kainic acid (2 $\mu$g in 1 $\mu$l of the physiological solution), that has been injected into striatum.

The control rats have been treated with an equal volume (1 $\mu$l) of the physiological solution.

After 7 days the rats have been sacrificed and the striatum has been removed. Each single determination has been performed with the pool of 5 samples. The gangliosides have been extracted and determined (as NANA content) as described previously.

Table 2 illustrates the results, showing that the treatment with CMP-NANA has hindered the diminuation of the level of gangliosides in the striatum determined by kainic acid.

TABLE 2

Levels of gangliosides measured and expressed as NANA content in the striatum of the rat. Values expressed as percentages related to the control, assumed as 100%; recovered cases as the medium of four pools of 5 samples each.

|  | Striatal gangliosides |
|---|---|
| Group 1: Control | 100 |
| Group 2: Administration of physiological solution | 96 |
| Group 3: Administration of kainic acid | 66 |
| Group 4: Administration of kainic acid and CMP-NANA | 88 |

EXAMPLE 3

Adsorption and distribution of the labeled CMP-NANA in the rat

CMP-NANA [9-$^3$H] has been purchased from NEN (New England Nuclear, 6072 Dreieich, West Germany).

The rats fasting for about 18 hours, have been treated with CMP-NANA, dissolved in the phosphate buffer, at the dose of 20 mg/kg i.m. (specific activity=1000 mCi/mg). After 30 min., 1 hour, 2 hours and 4 hours periods the animals have been sacrificed in the groups of 4, then liver, kidney and brain have been taken away from the animals and accurately weighted.

100 $\mu$g samples of the previous organs, and an analogous sample of the blood have been dissolved in Soluene 350 (Packard) and have been counted on the scintillation instrument in the liquid phase, on addition of the scintillating liquid.

The measurements have been quantized using a canal to canal-ratio technique. Table 3 illustrates the average results of all measurements. The radioactivity was rapidly diminished in the blood, and more slowly in the organs. The brain has demonstrated a radioactivity level inferior to those of the liver and kidney.

TABLE 3

Radioactivity levels in certain organs of the rat following the treatment with [$^3$H]-labeled CMP-NANA (20 mg/kg, i.m.). Average values from the 4 experiments expressed as the percentages of the administered dose and referred to 1 ml or 1 g of tissue.

|  | 30 min | 1 hr | 2 hrs | 4 hrs |
|---|---|---|---|---|
| Blood | 12.2 | 5.7 | 3.2 | 1.9 |
| Liver | 3.9 | 4.7 | 2.8 | 0.9 |
| Kidney | 2.6 | 5.2 | 3.3 | 1.6 |
| Brain | 6.2 | 7.8 | 4.9 | 2.4 |

EXAMPLE 4

CMP-NANA-Induced Neurite Formation in Cultured Cells

Neuro-2a cells (American Type Culture Collection, Rockville, USA) were seeded at standard conditions ($10^4$–$10^6$ cells/100 mm dish). After 12–24 hours CMP-NANA was added, with the concentrations indicated in Table 4. Incubation time for quantification of sprouting was 24 hours. Thereafter fixation of the cells was performed by means of 3% glutaraldehyde containing buffered saline. Quantitative determination of nerve cell growth was performed with Zeiss D-7082 Micreo-Videomat.

Neurite sprouting was used as the parameter for nerve cell differentiation. The samples fixed in formaline were stained for better contrast. A close dose-response relationship has been observed between the amount of CMP-NANA added and the number of neurites protruding from the cells (Table 4).

TABLE 4

Dose-response relationship of CMP-NANA-induced sprouting in Neuro-2a-cells

| Concentration of CMP-NANA (μg/ml) | Extent of sprouting |
|---|---|
| 0 | 100 ± 15 |
| 5 | 110 ± 15 |
| 10 | 117 ± 20 |
| 20 | 132 ± 25 |
| 30 | 145 ± 30 |
| 50 | 178 ± 35 |

It is evident from Table 4 that a concentration of CMP-NANA at 30 μg/ml increased the sprouting of the nerves to nearly 50% of above the original steady-state value, while 50 μg/ml of CMP-NANA resulted in a nearly doubled sprouting of the nerves in the cultured cells.

EXAMPLE 5

CMP-NANA Mediated in vitro Neuronal Maturation

Neuro-2a neurine neuroblastoma (American Type Culture Collection - CCL 131) was grown in the medium consisting of fecal calf serum (Irvine Scientific, Irvine, Calif.), to which non-essential amino acids, antibiotic (5-20 mg %), and bicarbonate (50-100 mg %), were added. The cells were grown routinely on corning plastic tissue culture flasks.

Cells for assay were plated on corning plastic Petri dishes, in the medium with or without CMP-NANA. In order to examine the role of CMP-NANA on in vitro neuron maturation, it was incorporated into the culture media at the time of plating or 24 or 48 hours postplating. The mean number and length of cell processes were repeatedly determined for a minimum of 100 cells per treatment group, to provide a semiquantitative index of neuron maturation (Table 5).

Index of maturation (I.M.) in Table 5 is expressed as: I.M.=L.P.×N.P., where:

L.P. 10:=the length of process to nearest 10μ
N.P.=Total number of processes

The effects of the various concentrations of CMP-NANA were evaluated with high resolution Nomarski optics.

TABLE 5

The effect of CMP-NANA on morphology of neuroblastoma cells

| Concentration of CMP-NANA (μg/ml) | Index of maturation (I.M.) |
|---|---|
| Standard media (SM) | 10 ± 2 |
| SM + 1 μg/ml | 20 ± 5 |
| SM + 5 μg/ml | 45 ± 5 |
| SM + 10 μg/ml | 68 ± 10 |
| SM + 20 μg/ml | 92 ± 10 |

It is evident from Table 5 that a concentration of CMP-NANA at 2 μg/ml doubled I.M. (as defined above), while 20 μg/ml of CMP-NANA let to ten time higher I.M. as determined for standard media.

EXAMPLE 6

Preparation of the injections for intravenous administration

| Active ingredient | 0.5 mg |
|---|---|
| Apyrogenic mannitol | 50 mg |
| Disodium phosphate · 12 H$_2$O | 5 mg |
| Monopotassium phosphate | 1 mg |
| Apyrogenic water for injections to | 2.0 mg |

Preparation procedure:

Active ingredient, mannitol and the inorganic salts were dissolved in sterile water for injections, the final pH being 6.5-6.7. The solution is sparged with steril nitrogen and is then clarified by filtration through a membrane filter of the pore size 0.45μ, then it is packed into glass ampoules of 2 ml.

Lyophilization was performed in an adequate lyophilisator maintaining the freezing temperature between −58° C. and −60° C., and by the final heating up to 35° C.

The ampoules thus obtained are sealed under sterile nitrogen. The product was controlled by physicochemical properties, residual humidity, the CMP-NANA content, redissolution, sterility, absence of pyrogenic materials, and non-toxicity.

EXAMPLE 7

| Active ingredient | 1.0 mg |
|---|---|
| Apyrogenic mannitol | 50 mg |
| Bisodium phosphate · 12 H$_2$O | 0.5 mg |
| Monopotassium phosphate | 1 mg |
| Apyrogenic water for injections | 2.0 ml |

Preparation procedure:
As in Example 6.

We claim:

1. Method for treatment of patients having lesions of the peripheral or central nervous system, comprising administration to said patients of a therapeutically effective amount of CMP-NANA or a pharmaceutically acceptable composition thereof.

2. Method according to claim 1, wherein said patients show brain lesions.

* * * * *